(12) United States Patent
Bisgaier (10) Patent No.: US 10,028,926 B2
(45) Date of Patent: Jul. 24, 2018

(54) METHODS OF REDUCING RISK OF CARDIOVASCULAR DISEASE

(71) Applicant: GEMPHIRE THERAPEUTICS INC., Livonia, MI (US)

(72) Inventor: Charles L. Bisgaier, Ann Arbor, MI (US)

(73) Assignee: Gemphire Therapeutics Inc., Livonia, MI (US)

( * ) Notice: Subject to any disclaimer, the term of this patent is extended or adjusted under 35 U.S.C. 154(b) by 228 days.

(21) Appl. No.: 14/370,722

(22) PCT Filed: Jan. 4, 2013

(86) PCT No.: PCT/US2013/020317
§ 371 (c)(1),
(2) Date: Jul. 3, 2014

(87) PCT Pub. No.: WO2013/103842
PCT Pub. Date: Jul. 11, 2013

(65) Prior Publication Data
US 2015/0005386 A1  Jan. 1, 2015

Related U.S. Application Data

(60) Provisional application No. 61/584,002, filed on Jan. 6, 2012.

(51) Int. Cl.
*A61K 31/194* (2006.01)
*A61K 45/06* (2006.01)

(52) U.S. Cl.
CPC ............ *A61K 31/194* (2013.01); *A61K 45/06* (2013.01)

(58) Field of Classification Search
None
See application file for complete search history.

(56) References Cited

U.S. PATENT DOCUMENTS 5,648,387 A  7/1997  Bisgaier et al.
2004/0229954 A1  11/2004  MacDougall et al.
2009/0312355 A1  12/2009  Bachovchin et al.

FOREIGN PATENT DOCUMENTS

WO  1999/030704 A1  6/1999

OTHER PUBLICATIONS

Stein et al. Efficacy and safety of gemcabene as add-on to stable statin therapy in hypercholesterolemic patients. J. Clin. Lipidology 10, 1212-1222 (2016).*
Written Opinion of the International Searching Authority for Application PCT/US13/20317 dated Mar. 12, 2013.
European Search Report for Application 13733913.1 dated Jun. 19, 2015.
Harold E. Bays et al; "Effectiveness and Tolerability of a New Lipid-Altering Agent, Gemcabene, in Patients With Low Levels of High-Density Lipoprotein Cholesterol", The American Journal of Cardiology vol. 92 Sep. 1, 2003; pp. 538-543.
Mandema, Japp W., et al., "Model-Based Development of Gemcabene, a NEw Lipid-Altering Agent", The AAPS Journal. 2005. pp. E513-E522. vol. 7, No. 3.
PCT International Search Report PCT/US2013/020317, dated Mar. 12, 2013.
Zetia® Package Insert, Highlights of Prescribing Information, 32147054T, REV 21, Merck/Schering-Plough Pharmaceuticals, 23 pages.

* cited by examiner

*Primary Examiner* — Jeffrey S Lundgren
*Assistant Examiner* — Michael J Schmitt
(74) *Attorney, Agent, or Firm* — Honigman Miller Schwartz and Cohn LLP; Cynthia M. Bott; Jonathan P. O'Brien (57) ABSTRACT

Methods of lowering the plasma LDL-C levels in a patient on a stable dose of statin where the patient has an LDL-C level above treatment goal. Methods of decreasing a patient's risk for developing coronary heart disease or having a recurrent cardiovascular event wherein the patient is on a stable dose of statin and the patient has an LDL-C level above treatment goal.

27 Claims, 1 Drawing Sheet

METHODS OF REDUCING RISK OF CARDIOVASCULAR DISEASE

CROSS REFERENCE TO RELATED APPLICATION(S)

This application is a 35 USC § 371 United States National Phase Application of, and claims priority to, PCT International Application No, PCT/US2013/020317 filed Jan. 4, 2013, which claims the benefit under 35 USC § 119 of U.S. Provisional Application Ser. No. 61/584,002 filed Jan. 6, 2012. The entire content of each of the aforesaid applications is incorporated herein by reference.

BACKGROUND OF THE INVENTION

Of all human medical health conditions, cardiovascular diseases are the single largest cause of morbidity and death. It is well known that the blood contains lipoproteins. These are particles responsible for transporting non-aqueous lipids throughout the body, and are generally classified into four major categories with the associated general functions; chylomicrons, large triglyceride containing lipoproteins produced by the intestine during the processes of absorbing dietary fat, very low density lipoproteins (VLDL) triglyceride-rich lipoproteins produced by the liver and facilitates transport of triglycerides to muscle and adipose tissue for energy and storage, low density lipoproteins (LDL), cholesterol-rich particles that transport cholesterol to cells for growth, repair, production of bile acids, or for storage as cholesteryl esters as a reservoir of cholesterol for steroid production, and finally high density lipoprotein, a phospholipid-rich lipoprotein, that facilitates removal of excess cholesterol from cells. Each type of lipoprotein is comprised of polar and nonpolar lipids as well as amphipathic apolipoproteins.

Human epidemiologic and clinical studies have demonstrated the importance of low levels of LDL-cholesterol (LDL-C) in the prevention and treatment of cardiovascular diseases. And Epidemiologic evidence has also shown that high levels of HDL-cholesterol (HDL-C) play a role in preventing cardiovascular disease. It is also believed that low levels of very low density lipoprotein-cholesterol (VLDL-C) and plasma triglycerides are important in the prevention of cardiovascular diseases.

It is well known that reduction of LDL-C is an important aspect of medical treatment to prevent or delay the onset of cardiovascular diseases as well as to treat existing cardiovascular diseases. More recently, it has been recognized that aggressive lowering of LDL-C is beneficial in delaying and preventing additional episodes of cardiovascular disease. Although LDL receives primary attention for clinical management, growing evidence indicates that other factors play important roles in determining risk for cardiovascular disease, for example, total cholesterol levels, HDL levels, blood pressure, and smoking status. Consideration of these risk factors is important in determining treatment goals. In particular, it is crucial for persons with known coronary heart disease (CHD) to control multiple risk factors responsible for the worsening of CHD.

Risk of cardiovascular disease is estimated in a variety of ways by a number of prognostic indicators. The Framingham Risk Score is based on data obtained from the Framingham Heart Study and is used to estimate the 10-year cardiovascular risk of an individual. The Framingham Risk Score is a calculated estimated risk for developing fatal or non-fatal cardiovascular event based on a composite score based on a pre-existing risk factors, including: age, gender, systolic blood pressure level (+/− treatment), HDL cholesterol level, and smoker status. A patient's risk score gives and indication of the likely benefits of prevention and also can be a useful metric to determine the effects of treatments.

The 2004-Updated National Cholesterol Education Program Adult Treatment Panel III (2004-Updated NCEP ATPIII) guidelines present treatment guidelines for patients with elevated LDL-C, triglycerides and other genetic or environmental risk factors. Briefly, the 2004-updated NCEP ATP III treatment guidelines recommend LDL-C lowering guidance based on pre-existing conditions. The updated guidelines add the use of Framingham projections of a 10-year absolute CHD risk to identify patients for more intensive treatment. For subjects with 0 or 1 risk factors, an LDL-C of less than 160 mg/dL is recommended. For subjects with two or more risk factors and with a Framingham 10-year risk of less than 10 percent, an LDL-C of less than 130 mg/dL is recommended. For subjects with two or more risk factors and with a Framingham 10-year risk of 10-20%, or existing cardiovascular heart disease, or cardiovascular heart disease risk equivalents, or a Framingham 10-year risk of greater than 20%, an LDL-C of less than 100 mg/dL is recommended. CHD risk equivalents include other clinical forms of atherosclerotic disease (peripheral arterial disease, abdominal aortic aneurysm, and symptomatic carotid artery disease); diabetes; and the presence of multiple risk factors that confer a 10-year Framingham risk for CHD of ≥20%. For subjects with established cardiovascular disease and also are diabetic, or are also smokers, or also have low levels of HDL-C and high levels of blood triglycerides, or also have metabolic syndrome, or also have multiple risk factors, an LDL-C of less than 70 mg/dL is recommended.

The difficulty of lowering the LDL-C level to less than 100 mg/dL or less in patients with known CHD has been well documented. Achieving the updated NCEP ATP-III guidelines recommendation to reduce LDL-C levels to lower than 70 mg/dL for persons at very high risk, is even more difficult.

In Europe, the Third Joint European Task Force (TJETF) provides recommendations or guidelines for lowering LDL-C based on existing LDL-C levels, total cholesterol levels, type 2 diabetes, systolic blood pressure, diastolic blood pressure, 10-year risk score of a fatal cardiovascular event, or preexisting atherosclerotic disease. Recommendations are also provided for patients having a combination of conditions, such as a known 10-year risk score of fatal cardiovascular disease plus elevated plasma total cholesterol or LDL cholesterol levels. Specifically the TJETF recommends reaching an LDL-C of less than 115 mg/dL if a subject's 10-year risk of cardiovascular disease is less than 5 percent, or has a 10-year risk of cardiovascular disease of greater than or equal to 5 percent and also has an existing total cholesterol of greater than or equal to 190 mg/dL or an existing LDL-C of greater than or equal to 115 mg/dL. The TJETF guidelines recommends reaching an LDL-C of less than 100 mg/dL if a subject has atherosclerotic disease, or Type 2 diabetes, or a total cholesterol greater than or equal to 320 mg/dL, or an LDL-C greater than or equal to 240 mg/dL, or has systolic blood pressure of greater than or equal to 180 mm Hg, or has diastolic blood pressure of greater than or equal to 110 mm Hg, or has a 10-year risk of cardiovascular disease of greater than or equal to 5 percent plus a total cholesterol of less than 190 mg/dL and an LDL-C less than 115 mg/dL.

Although statins are drugs of choice to lower LDL-C, not all patients can tolerate statins or can tolerate a high statin dose. In addition, approximately half of all patients on stable statin doses do not reach recommended LDL-C lowering goals, (See, *Centralized Pan-European Survey on the Undertreatment of Hypercholesterolemia in Patient Using Lipid Lowering Drugs, The Cepheus-Greece Survey*, Angiology (2010), Vol. 61 (5), pp 465-474 and the 2004-updated NCEP ATPIII guidelines.).

Furthermore, it is well recognized, that the doubling of a statin dose in a patient already on a statin, has limited effect on further LDL-C lowering while increasing safety issues associated with a high statin dose. The literature teaches that lowering cholesterol beyond that achieved with a stable statin dose is difficult. McKenney reported that statins have a nonlinear dose-response relationship such that doubling the dose of a particular statin provides only an additional 6% further lowering of LDL-C (American Journal of Therapeutics (2004), Vol. 11, pp 55-59). While other treatments can further lower LDL-C, this further reduction is often not enough to bring these patients' LDL-C level down to goal. For example, the combination of a stain plus a fibrate, such as fenofibrate has little effect or has a negative effect on LDL-C beyond the statin alone. The combinations of stains with bile acid sequestrants, such as cholestyramine, can result in lower LDL-C, however the reduction is often insufficient to reach a desirable LDL-C goal and compliance for bile acid sequestrants with patients is poor. Although agents such as Zetia, that block cholesterol absorption from the intestine, have shown improved LDL-C lowering when given with a statin, further lowering of LDL-C levels may be needed.

The goal for LDL-C levels under the current guidelines is guided by an assessment of the risk for developing cardiovascular heart disease or having a recurrence of a cardiovascular event.

Therefore there is a need for additional agents to reduce a patients risk for developing cardiovascular heart disease or having a recurrence of a cardiovascular event.

SUMMARY OF THE INVENTION

Unexpectedly, we found that in patients unable to reach the recommended goals for LCL-C levels with statin treatment alone, the addition of gemcabene resulted in a significant further reduction in plasma LDL-C levels and reduction in risk based on Framingham Risk scores.

The present invention relates to additional intervention in a patient group wherein despite being on a stable dose of a statin, the patients in the group have failed to achieve the relevant LDL cholesterol treatment goal or continue to have a high-risk for developing coronary heart disease or experiencing a recurrent cardiac event. With respect to the present invention the additional intervention comprises administering a compound of formula (I), formula (II), or formula (III) alone or in conjunction with another cholesterol lowering drug. These compounds are administered in conjunction with ongoing statin treatment. The addition of a compound of the invention to the ongoing statin treatment further reduces the LDL-C and results in a lowered risk for developing cardiovascular disease or having a recurrent cardiovascular event when compared to the level achieved in the absence of the compound of the invention.

Thus, one embodiment of the invention is a method of decreasing a patient's risk for developing coronary heart disease or having a recurrent cardiovascular event, comprising administering to the patient, an effective amount of a compound of formula (I):

wherein n, m, $R_1$, $R_2$, $R_3$, $R_4$, $Y_1$, and $Y_2$, are as defined herein, or an ester or a salt thereof, or a precursor thereof that metabolizes in vivo to the compound of formula (I) or the free acid, a salt, or a hydrate thereof; wherein the patient is on a stable dose of statin and the patient has an LDL-C level above treatment goal.

Another embodiment is a method of preventing, delaying the onset of, or reducing the severity of a secondary cardiovascular event comprising administering to a patient in need thereof, an effective amount of a compound of formula (I):

wherein n, m, $R_1$, $R_2$, $R_3$, $R_4$, $Y_1$, and $Y_2$, are as defined herein, or an ester or a salt thereof, or a precursor thereof that metabolizes in vivo to the compound of formula (I) or the free acid, a salt, or a hydrate thereof; wherein the patient is on a stable dose of statin and the patient has an LDL-C level above treatment goal.

Another embodiment of the invention is a method of lowering LDL-C level in a patient on a stable dose of statin, the patient having an LDL-C level above treatment goal, comprising administering to the patient, an effective amount of a compound of formula (I):

wherein n, m, $R_1$, $R_2$, $R_3$, $R_4$, $Y_1$, and $Y_2$ are as defined herein, or an ester or a salt thereof, or a precursor thereof that metabolizes in vivo to the compound of formula (I) or the free acid, a salt, or a hydrate thereof.

Additional embodiments are described herein.

DETAILED DESCRIPTION OF THE INVENTION

Figure 1:
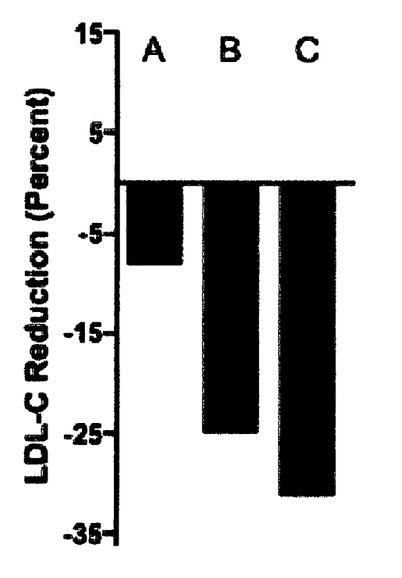
FIG. 1. Shows the additional lowering of LDL-C levels in patients not reaching treatment goals on statin alone resulting from the addition of gemcabene. Bar A of the graph represents statin treatment alone; B represents statin+300 mg gemcabene; and C represents statin+900 mg gemcabene.

As used herein, the term "carboxyalkylether" includes the free acid, pharmaceutically acceptable salts and esters thereof, and prodrugs thereof that are converted to the free acid, or salt or hydrate thereof. Such compounds are known in the art, as well as their synthesis and formulation.

"Subject" or "Patient" are used interchangeably.

The term "treating" or other forms of the word such as "treatment", or "treat" is used herein to mean that administration of a compound of the present invention mitigates a disease or a disorder in a host and/or reduces, inhibits, or eliminates a particular characteristic or event associated with a disorder (e.g., reduced steroidogenesis). Thus, the term "treatment" includes, preventing a disorder from occurring in a host, particularly when the host is predisposed to acquiring the disorder; inhibiting the disorder; and/or alleviating or reversing the disorder. Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state be completely avoided.

"HDL-C" is an abbreviation for high density lipoprotein cholesterol.

"LDL-C" is an abbreviation for low density lipoprotein cholesterol.

"LDL-C level" is used interchangeably with "plasma LDL-C level".

"VLDL-C" is an abbreviation for very low density lipoprotein cholesterol.

Throughout the description and claims of this specification the word "comprise" and other forms of the word, such as "comprising" and "comprises," means including but not limited to, and is not intended to exclude, for example, other additives, components, integers, or steps.

As used herein, the singular forms "a", "an", and "the" include plural references unless the context clearly dictates otherwise.

"Between" as used herein is inclusive, e.g., "between 1 mg and 5000 mg" includes 1 mg and 5000 mg.

"About" when used in conjunction with a number includes the number itself, for example, "from about 1 mg to about 5000 mg" includes the range "from 1 mg to 5000 mg".

"From" as used herein is inclusive, e.g., "from 1 mg to 5000 mg" includes 1 mg and 5000 mg.

"Alkyl" means a saturated aliphatic hydrocarbon containing 1-6 carbon atoms. An alkyl can be straight or branched.

"Alkenyl" means an aliphatic carbon that contains 2-6 carbon atoms and at least one double bond. Like an alkyl, an alkenyl can be straight or branched.

"Alkynyl" means an aliphatic carbon that contains 2-6 carbon atoms and at least one triple bond. Like an alkyl, an alkynyl can be straight or branched.

The term "carbocyclic ring" encompasses cycloalkyl and cycloalkenyl rings. Carbocyclic rings can be optionally substituted with one or more substituents such as aliphatic (e.g., alkyl, alkenyl, or alkynyl).

An "effective amount" is that amount of the compound, or pharmaceutically acceptable composition thereof, which is effective to lower plasma LDL-C levels and/or to reduce a patient's Framingham Risk Score.

"CHD" is an abbreviation for Coronary Heart Disease.

Reference to "a patient on a stable dose of a statin" means that the patient has been treated with a statin for a period sufficient for one of skill in the art to determine that the patient has reached a stable LDL-C level at a defined dose of a statin.

Patients at high risk for CHD or a recurrent cardiac event, include without limitation, persons with CHD (history of myocardial infarction, unstable angina, stable angina, coronary artery procedures, (such as angioplasty or bypass surgery, or evidence of clinically significant myocardial ischemia)) or CHD risk equivalents which include clinical manifestations of non-coronary forms of atherosclerotic disease, (such as peripheral arterial disease, abdominal aortic aneurysm, and carotid artery disease), diabetes, with 2 or more risk factors and a Framingham 10-year risk of developing CHD greater than 20%.

Patients at very high-risk for CHD or a recurrent cardiovascular event, include patients that have had a recent heart attack, or those who have cardiovascular disease combined with either diabetes, or severe or poorly controlled risk factors (such as continued smoking), or metabolic syndrome.

Cardiovascular diseases include, without limitation, coronary artery disease, cerebral vascular disease, such as stroke, peripheral vascular disease, or any diseases pertaining to an abnormal condition of the heart or circulatory system.

"Plasma LDL-C level" and "LDL-C level" are used interchangeably herein.

Statins are drugs that inhibit 3-hydroxymethylglutaryl coenzyme A reductase (HMG CoA reductase).

In 2002, the National Cholesterol Education Program (NCEP) published a report on detection, evaluation, and treatment of high blood cholesterol in Adults (NCEP ATP III) (NIH Publication No. 02-5215). In 2004, the NCEP issued updated recommendations (updated National Cholesterol Education Program Adult Treatment Panel III (2004-Updated NCEP ATPIII) guidelines). Treatment goals as defined in the updated guidelines are based on a patient's estimated risk for developing CHD. In summary, the goal for high-risk patients having CHD or a CHD risk equivalent, is an LDL-C level of less than 100 mg/dL. The goal for patients having two or more risk factors, is an LDL-C level of less than 130 mg/dl. The goal for patients having zero or one risk factor, the goal is an LDL-C level of less than 160 mg/dL. For very high-risk patients there is a therapeutic option where the recommended goal is an LDL-C level of less than 70 mg/dL. Risk factors include smoking, hypertension (Blood pressure of a 140/90 mmHg or on antihypertensive medication), low HDL cholesterol (<40 mg/dL), family history of premature CHD (CHD in male first degree relative <55 years; CHD in female first degree relative <65 years), and age (men ≥45 years; women ≥55 years). Patients with very high-risk are those who have had a recent heart attack, or those who have cardiovascular disease combined with either diabetes, or severe or poorly controlled risk factors (such as continued smoking), or metabolic syndrome.

A patient achieves an LDL cholesterol treatment goal when the patient's LDL-C level meets a recommended level as defined by the 2004-Updated NCEP ATPIII guidelines.

As used herein, references to 10-year risk are calculated using the Framingham point scores as provided in Tables 1 and 2, for men and women respectively.

TABLE 1

Estimate of 10-Year Risk for Men (Framingham Point Score)

| Age | Points |
| --- | --- |
| 20-34 | −9 |
| 35-39 | −4 |
| 40-44 | 0 |
| 45-49 | 3 |
| 50-54 | 6 |

TABLE 1-continued

Estimate of 10-Year Risk for Men (Framingham Point Score)

|  |  |  |  |  |  |
|---|---|---|---|---|---|
| 55-59 | 8 | | | | |
| 60-64 | 10 | | | | |
| 65-69 | 11 | | | | |
| 70-74 | 12 | | | | |
| 75-79 | 13 | | | | |

| Total | Points | | | | |
|---|---|---|---|---|---|
| Cholesterol | Age 20-39 | Age 40-49 | Age 50-59 | Age 60-69 | Age 70-79 |
| <160 | 0 | 0 | 0 | 0 | 0 |
| 160-199 | 4 | 3 | 2 | 1 | 0 |
| 200-239 | 7 | 5 | 3 | 1 | 0 |
| 240-279 | 9 | 6 | 4 | 2 | 1 |
| ≥280 | 11 | 8 | 5 | 3 | 1 |
| Nonsmoker | 0 | 0 | 0 | 0 | 0 |
| Smoker | 8 | 5 | 3 | 1 | 1 |

| HDL (mg/dL) | Points |
|---|---|
| ≥60 | -1 |
| 50-59 | 0 |
| 40-49 | 1 |
| <40 | 2 |

| Systolic BP (mmHg) | If Untreated | If Treated |
|---|---|---|
| <120 | 0 | 0 |
| 120-129 | 0 | 1 |
| 130-139 | 1 | 2 |
| 140-159 | 1 | 2 |
| ≥160 | 2 | 3 |

| Point Total | 10-Year Risk % |
|---|---|
| <0 | <1 |
| 0 | 1 |
| 1 | 1 |
| 2 | 1 |
| 3 | 1 |
| 4 | 1 |
| 5 | 2 |
| 6 | 2 |
| 7 | 3 |
| 8 | 4 |
| 9 | 5 |
| 10 | 6 |
| 11 | 8 |
| 12 | 10 |
| 13 | 12 |
| 14 | 16 |
| 15 | 20 |
| 16 | 25 |
| ≥17 | ≥30 |

TABLE 2

Estimate of 10-Year Risk for Women (Framingham Point Score)

| Age | Points |
|---|---|
| 20-34 | -7 |
| 35-39 | -3 |
| 40-44 | 0 |
| 45-49 | 3 |
| 50-54 | 6 |
| 55-59 | 8 |
| 60-64 | 10 |
| 65-69 | 12 |
| 70-74 | 14 |
| 75-79 | 16 |

| Total | Points | | | | |
|---|---|---|---|---|---|
| Cholesterol | Age 20-39 | Age 40-49 | Age 50-59 | Age 60-69 | Age 70-79 |

TABLE 2-continued

Estimate of 10-Year Risk for Women (Framingham Point Score)

| | | | | | |
|---|---|---|---|---|---|
| <160 | 0 | 0 | 0 | 0 | 0 |
| 160-199 | 4 | 3 | 2 | 1 | 1 |
| 200-239 | 8 | 6 | 4 | 2 | 1 |
| 240-279 | 11 | 8 | 5 | 3 | 2 |
| ≥280 | 13 | 10 | 7 | 4 | 2 |
| Nonsmoker | 0 | 0 | 0 | 0 | 0 |
| Smoker | 9 | 7 | 4 | 2 | 1 |

| HDL (mg/dL) | Points |
|---|---|
| ≥60 | -1 |
| 50-59 | 0 |
| 40-49 | 1 |
| <40 | 2 |

| Systolic BP (mmHg) | If Untreated | If Treated |
|---|---|---|
| <120 | 0 | 0 |
| 120-129 | 1 | 3 |
| 130-139 | 2 | 4 |
| 140-159 | 3 | 5 |
| ≥160 | 4 | 6 |

| Point Total | 10-Year Risk % |
|---|---|
| <9 | <1 |
| 9 | 1 |
| 10 | 1 |
| 11 | 1 |
| 12 | 1 |
| 13 | 2 |
| 14 | 2 |
| 15 | 3 |
| 16 | 4 |
| 17 | 5 |
| 18 | 6 |
| 19 | 8 |
| 20 | 11 |
| 21 | 14 |
| 22 | 17 |
| 23 | 22 |
| 24 | 27 |
| ≥25 | ≥30 |

The present invention relates to additional intervention in a patient group wherein despite being on a stable dose of a statin the patients in the group have failed to achieve the relevant LDL cholesterol treatment goal. With respect to the present invention, the additional intervention comprises administering a compound of formula (I), formula (II), or formula (III) alone or in conjunction with another cholesterol lowering drug. These compounds of formula (I), formula (II), or formula (III) are referred to throughout the specification and claims as "compounds of the present invention" or "compounds useful in the present invention".

In addition to LDL-C, other molecules play a role in the regulation of cholesterol. For example, ABCA1 is a cell membrane protein responsible for the transfer of cholesterol to HDL and thus plays a function in the assembly of HDL. ABCA1 deficiency is the metabolic basis of Tangier's disease which is characterized by low levels of HDL cholesterol, accumulation of lipid in organs, and premature atherosclerosis. Increased expression of ABCA1 can result in elevation of HDL cholesterol and reduced cardiovascular disease progression. PCSK9 is an LDL receptor associated protein that allows the receptor to undergo degradation following endocytosis. Binding PCSK9 with specific monoclonal antibodies allows recycling of the LDL receptor leading to a more efficient removal of LDL cholesterol. Targeting PCSK9 using DNA, antisense oligonucleotides, siRNA, microRNA, or small molecule inhibitors may also lead to reduced LDL cholesterol levels. PCSK9 inhibitors are known in the art, including but not limited to AMG 145 (Amgen), RN316 (Pfizer/Rlnat), RG7652 (Roche/Genentec), REGN727 (Sanofi/Regeneron). Therefore, one embodiment is a method of lowering the plasma LDL-C level in a patient on a stable dose of statin, the patient having an LDL-C level above treatment goal, comprising administering to the patient, an effective amount of a compound of formula (I) in combination with a PCSK9 inhibitor. Another embodiment is a method of decreasing a patient's risk for developing coronary heart disease or having a recurrent cardiovascular event, comprising administering to the patient an effective amount of a compound of formula (I) in combination with a PCSK9 inhibitor. Yet another embodiment is a method of preventing, delaying the onset of, or reducing the severity of a secondary cardiovascular event, comprising administering to a patient in need thereof, an effective amount of a compound of formula (I) in combination with a PCSK9 inhibitor.

In addition, ABCA1 elevating compounds are known, see for example U.S. Pat. No. 7,579,504, which is hereby incorporated by reference in its entirety. Embodiments of the invention therefore include embodiments wherein a compound of the present disclosure is administered in combination with an agent that elevates ABCA1 levels.

Several groups have disclosed that MicroRNAs play important roles in regulating cholesterol and fatty acid metabolism. MicroRNA are short non-coding RNAs that act as post-transcriptional regulators. A number of microRNAs have been identified. In particular, miR-33 has been shown to inhibit the expression of ABCA1. Targeted inhibition of microRNA-33 results in increased expression of ABCA1, elevated HDL cholesterol, and inhibition of atherosclerosis in mice. (see Rayner et al., Science vol. 328, 2010) In non-human primates, targeted inhibition of microRNA-33 results in elevated HDL-C and reduced LDL-C. Embodiments of the invention therefore include embodiments wherein a compound of the present disclosure is administered in combination with an agent that inhibits miR-33.

Another protein involved in cholesterol metabolism is Microsomal Transfer Protein-1 (MTP-1) which is an intracellular protein that facilitates the transfer of triglycerides to chylomicrons and VLDL during their assembly. The genetic deficiency of MTP-1 is the metabolic basis of the abetalipoproteinemia. The production of apolipoprotein B100 or apolipoprotein B-48, which are derived from a single gene via post transcriptional processing, are used in the assembly of VLDL and chylomicrons, respectively, and are constitutively produced and act as a surplus for use as a ready source to assemble these particles given delivery of triglycerides via MTP-1. The lack or reduction of MTP-1 markedly inhibits triglyceride delivery to the assembly process and forces the degradation of apolipoprotein B-100 or B-48 and leads to accumulation of intracellular triglycerides. MTP-1 activity leads to a fatty liver and intestinal enterocyte accumulation of triglyceride-rich lipid droplets. Pharmacological inhibition of MTP-1 is being developed to decrease LDL production and to reduce levels of LDL-C in homozygous familial hypercholesterolemia. Embodiments of the invention therefore include embodiments wherein a compound of the present disclosure is administered in combination with an agent that inhibits MTP-1.

Depending on the dose of the compound of the invention that is administered to the patient on a stable dose of statin, the LDL-C level may be further lowered by at least 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70% or at least by about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, or about 70%.

In some embodiments administration of a compound of the invention to a patient on a stable dose of statin, the LDL-C level is further lowered by about 10% to about 20%, or from about 10% to about 30%, or from about 20% to about 40%, or from about 20% to about 50%, or from about 20% to about 60%, or from about 20% to about 70%, or from about 30% to about 70%, or from about 30% to about 80%, or from about 30% to about 90%, with respect to the amount LDL-C was lowered by the statin.

In one embodiment administration of a compound of the invention to a patient on a stable dose of statin, the LDL-C level is lowered to ≤240 mg/dL. In another embodiment the LDL-C level is lowered to ≤200 mg/dL. In yet another embodiment the LDL-C level is lowered to ≤150 mg/dL. In still another embodiment the LDL-C level is lowered to ≤140 mg/dL. In another embodiment the LDL-C level is lowered to ≤130 mg/dL. In yet another embodiment the LDL-C level is lowered to ≤115 mg/dL. In another embodiment the LDL-C level is lowered to ≤70 mg/dL.

It will be understood by one of skill in the art that any further reduction of LDL-C that brings the patient's LDL-C level closer to goal is desirable. It is not necessary that the combination of the statin and a compound of the invention lowers LDL-C to the treatment goal in order for the combination to be useful.

One embodiment of the invention is a method of lowering the plasma LDL-C level in a patient on a stable dose of statin, the patient having an LDL-C level above treatment goal, comprising administering to the patient, an effective amount of a compound of the present invention.

Another embodiment of the present invention is a method of lowering the plasma LDL-C level in a patient on a stable dose of statin, the patient having an LDL-C level above treatment goal, comprising administering to the patient, an effective amount of a compound of formula (I), formula (II) or formula (III), or an ester or a salt thereof, or a precursor thereof that metabolizes in vivo to the compound of formula (I), or the free acid, a salt, or a hydrate thereof.

One embodiment of the invention is a method of lowering the plasma LDL-C level in a patient on a stable dose of statin, the patient having an LDL-C level above treatment goal, comprising administering to the patient, an effective amount of a compound of formula (I):

(I)

wherein n, and m independently are integers from 2 to 9; each occurrence of $R_1$, $R_2$, $R_3$, and $R_4$ is independently $C_1$-$C_6$ alkyl, $C_2$-$C_6$ alkenyl, $C_2$-$C_6$ alkynyl, or $R_1$ and $R_2$, taken together with the carbon to which they are attached, form a carbocyclic ring having from 3 to 6 carbons, or $R_3$ and $R_4$ together with the carbon to which they are attached, form a carbocyclic ring having from 3 to 6 carbons; $Y_1$ and $Y_2$ independently are —COOH, —CH$_2$OH, tetrazole, and —COOR$_5$; $R_5$ is $C_1$-$C_6$ alkyl, $C_2$-$C_6$ alkenyl, $C_2$-$C_6$ alkynyl; or an ester or a salt thereof, or a precursor thereof that metabolizes in vivo to the compound of formula (I) or the free acid, a salt, or a hydrate thereof.

Another embodiment of the invention is a method of decreasing a patient's risk for developing coronary heart disease or having a recurrent cardiovascular event, comprising administering to the patient, an effective amount of a compound of the invention, wherein the patient is on a stable dose of statin and the patient has an LDL-C level above treatment goal. In particular embodiments, the risk score is accessed using the Framingham Risk Score equation. In one embodiment the patient's Framingham Risk Score is reduced by between about 1 and about 2 points when compared with treatment with statin alone. In another embodiment the patient's Framingham Risk Score is reduced by between about 2 and about 3 points when compared with treatment with statin alone. In another embodiment the patient's Framingham Risk Score is reduced by between about 3 and about 4 points when compared with treatment with statin alone. In yet another embodiment the patient's Framingham Risk Score is reduced by ≥1 point. In still another embodiment the patient's Framingham Risk Score is reduced by ≥2 points. In another embodiment the patient's Framingham Risk Score is reduced by ≥3 points. In another embodiment the patient's Framingham Risk Score is reduced by ≥4 points.

Another embodiment of the invention is a method of decreasing a patient's risk for developing coronary heart disease or having a recurrent cardiovascular event, comprising administering to the patient, an effective amount of a compound of formula (I), formula (II) or formula (III), or an ester or a salt thereof, or a precursor thereof that metabolizes in vivo to the compound of formula (I) or the free acid, a salt, or a hydrate thereof, wherein the patient is on a stable dose of statin and the patient has an LDL-C level above treatment goal.

Another embodiment of the invention is a method of decreasing a patient's risk for developing coronary heart disease or having a recurrent cardiovascular event, comprising administering to the patient, an effective amount of a compound of formula (I):

wherein n, and m independently are integers from 2 to 9; each occurrence of $R_1$, $R_2$, $R_3$, and $R_4$ is independently $C_1$-$C_6$ alkyl, $C_2$-$C_6$ alkenyl, $C_2$-$C_6$ alkynyl, or $R_1$ and $R_2$, taken together with the carbon to which they are attached, form a carbocyclic ring having from 3 to 6 carbons, or $R_3$ and $R_4$ together with the carbon to which they are attached, form a carbocyclic ring having from 3 to 6 carbons; $Y_1$ and $Y_2$ independently are —COOH, —CH$_2$OH, tetrazole, and —COOR$_5$; $R_5$ is $C_1$-$C_6$ alkyl, $C_2$-$C_6$ alkenyl, $C_2$-$C_6$ alkynyl; or an ester or a salt thereof, or a precursor thereof that metabolizes in vivo to the compound of formula (I) or the free acid, a salt, or a hydrate thereof; wherein the patient is on a stable dose of statin and the patient has an LDL-C level above treatment goal.

Another embodiment is a method of preventing, delaying the onset of, or reducing the severity of a secondary cardiovascular event comprising administering to a patient in need thereof, an effective amount of a compound of the present invention, wherein the patient is on a stable dose of statin and the patient has an LDL-C level above treatment goal.

Another embodiment is a method of preventing, delaying the onset of, or reducing the severity of a secondary cardiovascular event comprising administering to the patient, an effective amount of a compound of formula (I), formula (II) or formula (III), or an ester or a salt thereof, or a precursor thereof that metabolizes in vivo to the compound of formula (I) or the free acid, a salt, or a hydrate thereof, wherein the patient is on a stable dose of statin and the patient has an LDL-C level above treatment goal.

Yet another embodiment is a method of preventing, delaying the onset of, or reducing the severity of a secondary cardiovascular event comprising administering to a patient in need thereof, an effective amount of a compound of formula (I):

wherein n, and m independently are integers from 2 to 9; each occurrence of $R_1$, $R_2$, $R_3$, and $R_4$ is independently $C_1$-$C_6$ alkyl, $C_2$-$C_6$ alkenyl, $C_2$-$C_6$ alkynyl, or $R_1$ and $R_2$, taken together with the carbon to which they are attached, form a carbocyclic ring having from 3 to 6 carbons, or $R_3$ and $R_4$ together with the carbon to which they are attached, form a carbocyclic ring having from 3 to 6 carbons; $Y_1$ and $Y_2$ independently are —COOH, —CH$_2$OH, tetrazole, and —COOR$_5$; $R_5$ is $C_1$-$C_6$ alkyl, $C_2$-$C_6$ alkenyl, $C_2$-$C_6$ alkynyl; or an ester or a salt thereof, or a precursor thereof that metabolizes in vivo to the compound of formula (I) or the free acid, a salt, or a hydrate thereof; wherein the patient is on a stable dose of statin and the patient has an LDL-C level above treatment goal.

In some embodiments the compound of formula (I) is administered as a free acid. In other embodiments the compound administered is a pharmaceutically acceptable salt of a compound of formula (I). In yet other embodiments the compound administered is an ester of a compound of formula (I). In some embodiments the compound administered is a precursor (pro-drug) of formula (I) that metabolizes in vivo to the active carboxyalkylether acid or a salt of formula (I).

In some embodiments, the compound is a compound of formula I, wherein n is 2, or n is 3, or n is 4, or n is 5, or n is 6, or n is 7, or n is 8, or n is 9. In some embodiments, m is 2, or n is 3, or m is 4, or m is 5, or m is 6, or m is 7, or m is 8, or m is 9. In some embodiments, n and m are both 2, or n and m are both 3, or n and m are both 4, or n and m are both 5, or n and m are both 6, or n and m are both 7, or n and m are both 8, or n and m are both 9.

In some embodiments, the compound is a compound of formula I, wherein $R_1$, $R_2$, $R_3$, and $R_4$ independently are $C_1$-$C_6$ alkyl. In some embodiments $R_1$, $R_2$, $R_3$, and $R_4$ are all

$C_1$-$C_6$ alkyl. In some embodiments $R_1$, $R_2$, $R_3$, and $R_4$ independently are $C_2$-$C_6$ alkenyl. In some embodiments $R_1$, $R_2$, $R_3$, and $R_4$ independently are $C_2$-$C_6$ alkynyl. In some embodiments $R_1$, $R_2$, $R_3$, and $R_4$ are —$CH_3$. In some embodiments $R_1$, $R_2$, $R_3$, and $R_4$ are —$CH_2CH_3$. In some embodiments $R_1$, $R_2$, $R_3$, and $R_4$ are —$CH_2CH_2CH_3$. In some embodiments $R_1$, $R_2$, $R_3$, and $R_4$ are all $C_2$-$C_6$ alkenyl. In some embodiments $R_1$, $R_2$, $R_3$, and $R_4$ are all $C_2$-$C_6$ alkynyl. In some embodiments $R_1$ and $R_2$, taken together with the carbon to which they are attached, form a carbocyclic ring having from 3 to 6 carbons. In other embodiments $R_3$ and $R_4$, taken together with the carbon to which they are attached, form a carbocyclic ring having from 3 to 6 carbons.

In some embodiments, the compound is a compound of formula I, wherein $Y_1$ and $Y_2$ are both —COOH. In some embodiments $Y_1$ and $Y_2$ are both —$CH_2OH$. In some embodiments $Y_1$ and $Y_2$ are both -tetrazole. In some embodiments $Y_1$ and $Y_2$ are both —$CH_2(OH)$. In some embodiments $Y_1$ and $Y_2$ are both —$COOR_5$ and $R_5$ is $C_1$-$C_6$ alkyl. In some embodiments $Y_1$ and $Y_2$ are both —$COOR_5$ and $R_5$ is $C_2$-$C_6$ alkenyl. In some embodiments $Y_1$ and $Y_2$ are both —$COOR_5$ and $R_5$ is $C_2$-$C_6$ alkynyl.

In another embodiment, the compound is a compound of formula I, wherein n and m are the same integer, and $R_1$, $R_2$, $R_3$, and $R_4$ independently are $C_1$-$C_6$ alkyl. In yet another embodiment, the compound is a compound of formula I, wherein $Y_1$ and $Y_2$ are the same and are —COOH or —$COOR_5$, and $R_5$ is $C_1$-$C_6$ alkyl. In a preferred embodiment, the compound is a compound of formula I, wherein $Y_1$ and $Y_2$ are COOH, $R_1$, $R_2$, $R_3$, and $R_4$ are methyl, and n and m are the same and are an integer selected from 2, 3, 4, or 5, preferably n and m are the same and are 4 or 5. Most preferably n and m are 4. In still another embodiment, the compound is a compound of formula I, wherein $Y_1$, and $Y_2$ are —COOH, and $R_1$, $R_2$, $R_3$, and $R_4$ independently are $C_1$-$C_6$ alkyl, and n and m are 4. In another embodiment the compound is a compound of formula I, wherein $Y_1$ and $Y_2$ are —COOH, n and m are 4, $R_1$, $R_2$, $R_3$, and $R_4$ are methyl. In another embodiment the compound is a compound of formula I, wherein $Y_1$ and $Y_2$ are —COOH, n and m are 5, $R_1$, $R_2$, $R_3$, and $R_4$ are methyl. In yet another embodiment, the compound is a compound of formula I, wherein $Y_1$ and $Y_2$ are —$CH_2OH$, and n and m are 4. In another embodiment, the compound is a compound of formula I, wherein $Y_1$ and $Y_2$ are —$CH_2OH$, n and m are 4 and $R_1$, $R_2$, $R_3$, and $R_4$ are methyl.

Compounds of formula (I) can be referred to generally as carboxyalkylethers. Carboxyalkylethers are a class of compounds described by Bisgaier et al. in U.S. Pat. No. 5,648,387, and by Ando et al. in U.S. Pat. No. 6,861,555, both patents are incorporated herein by reference. These compounds are described as having a number of biological activities, including raising levels of high density lipoproteins (HDL), and are said to be useful for treating cardiovascular disorders, diabetes, and other medical conditions. The compounds can be used alone or in combination with other agents such as statins, for example as described by Bisgaier et al. in U.S. Patent Publication No. 2002/0103252, which is incorporated herein by reference.

In one embodiment of this invention, the compound of formula (I) is a compound known as "CI-1027", as "gemcabene", and as "PD 72953" (Bays et. al., Am. J. Cardiol. (2003); Vol. 92, pp 538-543, incorporated herein by reference). The chemical name of this compound is 6,6'-oxybis-(2,2'-dimethylhexanoic acid) or alternately 6-(5-carboxy-5-methyl-hexyloxy)-2,2-dimethylhexanoic acid.

(gemcabene)

In another embodiment gemcabene is administered as a pharmaceutical salt. In yet another embodiment, gemcabene is administered as a calcium salt.

In another embodiment gemcabene is administered as the anhydrous monocalcium salt. The structure of the anhydrous monocalcium salt of gemcabene is:

In an embodiment gemcabene is administered as a hydrate. In another embodiment gemcabene is administered as the hydrate of the monocalcium salt, as described in U.S. Pat. No. 6,861,555. The structure of the hydrate of the monocalcium salt of gemcabene is:

In another embodiment, gemcabene is administered in a crystalline form.

Another embodiment of the invention is a method of lowering the plasma LDL-C level in a patient on a stable dose of statin, the patient having an LDL-C level above treatment goal, comprising administering to the patient, an effective amount of gemcabene.

Another embodiment of the invention is a method of decreasing a patient's risk for developing coronary heart disease or having a recurrent cardiovascular event, comprising administering to the patient, an effective amount of gemcabene, wherein the patient is on a stable dose of statin and the patient has an LDL-C level above treatment goal.

Yet another embodiment is a method of preventing, delaying the onset of, or reducing the severity of a secondary cardiovascular event comprising administering to a patient in need thereof, an effective amount of gemcabene, wherein the patient is on a stable dose of statin and the patient has an LDL-C level above treatment goal.

Another embodiment of the invention is a method of lowering the plasma LDL-C level in a patient on a stable dose of statin, the patient having an LDL-C level above treatment goal, comprising administering to the patient, an effective amount of a calcium salt of gemcabene.

Another embodiment of the invention is a method of decreasing a patient's risk for developing coronary heart disease or having a recurrent cardiovascular event, comprising administering to the patient, an effective amount of a calcium salt of gemcabene, wherein the patient is on a stable dose of statin and the patient has an LDL-C level above treatment goal.

Yet another embodiment is a method of preventing, delaying the onset of, or reducing the severity of a secondary cardiovascular event comprising administering to a patient in need thereof, an effective amount of a calcium salt of gemcabene, wherein the patient is on a stable dose of statin and the patient has an LDL-C level above treatment goal.

Another embodiment of the invention is a method of lowering the plasma LDL-C level in a patient on a stable dose of statin, the patient having an LDL-C level above treatment goal, comprising administering to the patient, an effective amount of gemcabene-monocalcium salt.

Another embodiment of the invention is a method of decreasing a patient's risk for developing coronary heart disease or having a recurrent cardiovascular event, comprising administering to the patient, an effective amount of gemcabene-monocalcium salt, wherein the patient is on a stable dose of statin and the patient has an LDL-C level above treatment goal.

Yet another embodiment is a method of preventing, delaying the onset of, or reducing the severity of a secondary cardiovascular event comprising administering to a patient in need thereof, an effective amount of gemcabene-monocalcium salt, wherein the patient is on a stable dose of statin and the patient has an LDL-C level above treatment goal.

Therefore another embodiment of the invention is a method of lowering the plasma LDL-C level in a patient on a stable dose of statin, the patient having an LDL-C level above treatment goal, comprising administering to the patient, an effective amount of gemcabene or an ester or a salt thereof, or a precursor thereof that metabolizes in vivo to the compound, or the free acid, a salt, or a hydrate thereof.

Another embodiment of the invention is a method of decreasing a patient's risk for developing coronary heart disease or having a recurrent cardiovascular event, comprising administering to the patient, an effective amount of gemcabene or an ester or a salt thereof, or a precursor thereof that metabolizes in vivo to the compound of formula (I) or the free acid, a salt, or a hydrate thereof; wherein the patient is on a stable dose of statin and the patient has an LDL-C level above treatment goal.

Yet another embodiment is a method of preventing, delaying the onset of, or reducing the severity of a secondary cardiovascular event comprising administering to a patient in need thereof, an effective amount of gemcabene or an ester or a salt thereof, or a precursor thereof that metabolizes in vivo to the compound of formula (I) or the free acid, a salt, or a hydrate thereof; wherein the patient is on a stable dose of statin and the patient has an LDL-C level above treatment goal.

In another embodiment the compound of formula (I) is:

or a salt thereof. (See Mueller R. et al. J. Med. Chem., 2004, 47 (21), pp 5183-5197).

Another compound useful in the methods of the present invention is a compound known as ESP 55016 and alternately as ETC 1002. ESP 55016 which is described in Cramer, C. T., et al. J. Lipid Res. 2004, 45:1289-1301. The structure of ESP 55016 is:

ESP 55016 was shown to be effective in lowering non-HDL-C, raising HDL-C, and decreasing triglyceride levels in obese female Zucker rats. Also useful in the present invention are pharmaceutically acceptable salts or an ester of ESP 55016.

Therefore another embodiment of the invention is a method of lowering the plasma LDL-C level in a patient on a stable dose of statin, the patient having an LDL-C level above treatment goal, comprising administering to the patient, an effective amount of the compound:

or an ester or a salt thereof, or a precursor thereof that metabolizes in vivo to the compound, or the free acid, a salt, or a hydrate thereof.

Another embodiment of the invention is a method of decreasing a patient's risk for developing coronary heart disease or having a recurrent cardiovascular event, comprising administering to the patient, an effective amount of the compound:

or an ester or a salt thereof, or a precursor thereof that metabolizes in vivo to the compound of formula (I) or the free acid, a salt, or a hydrate thereof; wherein the patient is on a stable dose of statin and the patient has an LDL-C level above treatment goal.

Yet another embodiment is a method of preventing, delaying the onset of, or reducing the severity of a secondary cardiovascular event comprising administering to a patient in need thereof, an effective amount of the compound:

or an ester or a salt thereof, or a precursor thereof that metabolizes in vivo to the compound of formula (I) or the free acid, a salt, or a hydrate thereof; wherein the patient is on a stable dose of statin and the patient has an LDL-C level above treatment goal.

Other compounds useful in the methods of the present invention are compounds of formula (II):

(II)

wherein n and m are an integer from 3-5; each of $R_1$, $R_2$, $R_3$, and $R_4$ is independently methyl, phenyl, 4-methyl-phenyl, and 4-butyl-phenyl; $Y_1$ and $Y_2$ independently are —COOH, —$CH_2OH$, tetrazole, and —$COOR_5$; $R_5$ is $C_1$-$C_6$ alkyl, $C_2$-$C_6$ alkenyl, $C_2$-$C_6$ alkynyl; or an ester or a salt thereof.

Compounds of formula (II) have been disclosed and described as lipid lowering agent. (See Mueller R. et al., J. Med. Chem. (2004), Vol. 47 (21), pp 5183-5197)

Other compounds useful in the methods of the present invention are compounds of formula (III):

(III)

wherein n, and m independently are integers from 4 to 7; each occurrence of $R_1$, $R_2$, $R_3$, and $R_4$ is independently $C_1$-$C_6$ alkyl, $C_2$-$C_6$ alkenyl, $C_2$-$C_6$ alkynyl, or $R_1$ and $R_2$ taken together with the carbon to which they are attached, form a carbocyclic ring having from 3 to 6 carbons, or $R_3$ and $R_4$ together with the carbon to which they are attached, form a carbocyclic ring having from 3 to 5 carbons; R is H or $C_1$-$C_6$ alkyl; or an ester or a salt thereof, or a precursor thereof that metabolizes in vivo to the compound of formula (III) or the free acid, a salt, or a hydrate thereof.

Specific compounds of formula (III) include:

and salts or esters thereof, or a precursor thereof that metabolizes in vivo to the compound of formula (III) or the free acid, a salt, or a hydrate thereof.

Compounds of formula (III) have been disclosed and described as lipid lowering agents. (See Bell R. P. L. et al., Bioorg. Med. Chem. (2005), Vol. 13, pp 223-236 and Oniciu et al., J. Med. Chem. (2006), Vol. 49, No. 1, pp 334-348).

Compounds useful in the methods of the invention also include precursors or pro-drugs of the compounds of the present disclosure, namely compounds that when administered to a subject are metabolized or otherwise converted in vivo to the free acid, salt, or hydrate thereof. See Goel, U.S. Pat. No. 7,345,190 "Carnitine conjugates as dual prodrugs and uses thereof", incorporated herein by reference. Other compounds that are metabolized in situ include those described in U.S. Pat. Nos. 6,410,802, 6,459,003, 6,645,170, 6,713,507, 6,790,953 and 7,192,940, all of which are incorporated herein by reference.

In some cases patients may be or may become intolerant or resistant to statin therapy. In some cases the patient experience adverse events, for example, muscle pain, myopathy or rhabdomyloysis, increased levels of serum alanine aminotransferase (ALT). In such cases, statin use may be contraindicated. It is contemplated that for these patients, monotherapy with the compounds of the invention can be administered and LDL-C lowering achieved. In general, adverse events associated with statins increase in frequency and severity with increasing dose of statin.

In some cases a patient receiving a statin may not achieve goal because the patient is being treated at the maximum dose of statin tolerated by that patient which is insufficient to obtain the desired result. The compounds of the invention are contemplated for use in such patients. One of skill in the art would understand that combination treatment of a statin and a compound of the invention could be useful in further lowering LDL-C while the patient is treated at the maximum tolerated dose of statin even where that dose is lower than the maximum allowed dose.

It is contemplated that any of the foregoing method can be used to treat a patient with one or more of the following conditions: coronary heart disease or a coronary heart risk equivalent, or has had a previous primary cardiovascular event, or a previous cerebral vascular event. Or the patient is being treated by any of the methods of the disclosure has as a risk factor, smokes, has hypertension, is undergoing treatment with an antihypertensive medication, has an HDL cholesterol level less than 40 mg/dL, has a family history of premature coronary heart disease, is a male ≥45 years or a female ≥55 years of age.

One embodiment is a method of lowering the plasma LDL-C level in a patient on a stable dose of statin, wherein the patient has a 10-year risk for coronary heart disease of ≥10%, or ≥20%, or ≥25%, or ≥30%, comprising administering to the patient, an effective amount of a compound of formula (I). Another embodiment is a method of decreasing a patient's risk for developing coronary heart disease or having a recurrent cardiovascular event, wherein the patient has a 10-year risk for coronary heart disease of ≥10%, or ≥20%, or ≥25%, or ≥30%, comprising administering to the patient an effective amount of a compound of formula (I). Yet another embodiment is a method of preventing, delaying the onset of, or reducing the severity of a secondary cardiovascular event, wherein the patient has a 10-year risk for coronary heart disease of ≥10%, or ≥20%, or ≥25%, or ≥30%, comprising administering to the patient an effective amount of a compound of formula (I).

One embodiment is a method of lowering the plasma LDL-C level in a patient on a stable dose of statin, wherein the patient has an LDL-C level of ≥70 mg/dL, or ≥100 mg/dL, or ≥115 mg/dL, or ≥130 mg/dL, or ≥160 mg/dL, or ≥240 mg/dL, comprising administering to the patient, an effective amount of a compound of formula (I). Another embodiment is a method of decreasing a patient's risk for developing coronary heart disease or having a recurrent cardiovascular event, wherein the patient has an LDL-C level of ≥70 mg/dL, or ≥100 mg/dL, or ≥115 mg/dL, or ≥130 mg/dL, or ≥160 mg/dL, or ≥240 mg/dL, comprising administering to the patient an effective amount of a compound of formula (I). Yet another embodiment is a method of preventing, delaying the onset of, or reducing the severity of a secondary cardiovascular event, wherein the patient has an LDL-C level of ≥70 mg/dL, or ≥100 mg/dL, or ≥115 mg/dL, or ≥130 mg/dL, or ≥160 mg/dL, or ≥240 mg/dL, comprising administering to the patient an effective amount of a compound of formula (I).

Another embodiment is a method of lowering the plasma LDL-C level in a patient on a stable dose of statin, wherein the patient has an LDL-C level between about 70 mg/dL and about 100 mg/dL, or between about 70 mg/dL and about 115 mg/dL, or between about 115 mg/dL and about 130 mg/dL, or between about 130 mg/dL and about 160 mg/dL, or between about 160 mg/dL and about 240 mg/dL, comprising administering to the patient, an effective amount of a compound of formula (I). Another embodiment is a method of decreasing a patient's risk for developing coronary heart disease or having a recurrent cardiovascular event, wherein the patient has LDL-C level between about 70 mg/dL and about 100 mg/dL, or between about 70 mg/dL and about 115 mg/dL, or between about 115 mg/dL and about 130 mg/dL, or between about 130 mg/dL and about 160 mg/dL, or between about 160 mg/dL and about 240 mg/dL, comprising administering to the patient an effective amount of a compound of formula (I). Yet another embodiment is a method of preventing, delaying the onset of, or reducing the severity of a secondary cardiovascular event, wherein the patient has an LDL-C level between about 70 mg/dL and about 100 mg/dL, or between about 70 mg/dL and about 115 mg/dL, or between about 115 mg/dL and about 130 mg/dL, or between about 130 mg/dL and about 160 mg/dL, or between about 160 mg/dL and about 240 mg/dL, comprising administering to the patient an effective amount of a compound of formula (I).

Another embodiment is a method of lowering the plasma LDL-C level in a patient on a stable dose of statin, wherein the patient is diabetic, comprising administering to the patient, an effective amount of a compound of formula (I). Another embodiment is a method of decreasing a patient's risk for developing coronary heart disease or having a recurrent cardiovascular event, wherein the patient is diabetic, comprising administering to the patient an effective amount of a compound of formula (I). Yet another embodiment is a method of preventing, delaying the onset of, or reducing the severity of a secondary cardiovascular event, wherein the patient is diabetic, comprising administering to the patient an effective amount of a compound of formula (I).

Another embodiment is one embodiment is a method of lowering the plasma LDL-C level in a patient on a stable dose of statin, wherein the patient has an HDL cholesterol level less than 40 mg/dL and blood triglycerides levels ≥150 mg/dL, comprising administering to the patient, an effective amount of a compound of formula (I). Another embodiment is a method of decreasing a patient's risk for developing coronary heart disease or having a recurrent cardiovascular event, wherein the patient has an HDL cholesterol level less than 40 mg/dL and blood triglycerides levels ≥150 mg/dL, comprising administering to the patient an effective amount of a compound of formula (I). Yet another embodiment is a method of preventing, delaying the onset of, or reducing the severity of a secondary cardiovascular event, wherein the patient has an HDL cholesterol level less than 40 mg/dL and blood triglycerides levels ≥150 mg/dL, comprising administering to the patient an effective amount of a compound of formula (I).

Another embodiment is one embodiment is a method of lowering the plasma LDL-C level in a patient on a stable dose of statin, wherein the patient has metabolic syndrome, comprising administering to the patient, an effective amount of a compound of formula (I). Another embodiment is a method of decreasing a patient's risk for developing coronary heart disease or having a recurrent cardiovascular event, wherein the patient has metabolic syndrome, comprising administering to the patient an effective amount of a compound of formula (I). Yet another embodiment is a method of preventing, delaying the onset of, or reducing the severity of a secondary cardiovascular event, wherein the patient has metabolic syndrome, comprising administering to the patient an effective amount of a compound of formula (I).

Another embodiment is one embodiment is a method of lowering the plasma LDL-C level in a patient on a stable dose of statin, wherein the patient is administered one or more additional cholesterol lowering drugs independently selected from a cholesterol absorption inhibitor, a bile acid sequestrant, a cholesteryl ester transfer protein inhibitor, a microsomal triglyceride transfer protein inhibitor, a miR-33 inhibitor, a PCSK9 inhibitor, a squalene synthase inhibitor and an apoB synthesis inhibitor, comprising administering to the patient, an effective amount of a compound of formula (I). Another embodiment is a method of decreasing a patient's risk for developing coronary heart disease or having a recurrent cardiovascular event, wherein the patient is administered one or more additional cholesterol lowering drugs independently selected from a cholesterol absorption inhibitor, a bile acid sequestrant, a cholesteryl ester transfer protein inhibitor, a microsomal triglyceride transfer protein inhibitor, a miR-33 inhibitor, a PCSK9 inhibitor, a squalene synthase inhibitor and an apoB synthesis inhibitor, comprising administering to the patient an effective amount of a compound of formula (I). Yet another embodiment is a method of preventing, delaying the onset of, or reducing the severity of a secondary cardiovascular event, wherein the patient is administered one or more additional cholesterol lowering drugs independently selected from a cholesterol absorption inhibitor, a bile acid sequestrant, a cholesteryl ester transfer protein inhibitor, a microsomal triglyceride transfer protein inhibitor, a miR-33 inhibitor, a PCSK9 inhibitor, a squalene synthase inhibitor, and an apoB synthesis inhibitor, comprising administering to the patient an effective amount of a compound of formula (I).

In some embodiments the additional cholesterol lowering drug is ezetimibe, cholestyramine, or Vytorin.

The effective daily dose of a compound of the present invention is typically from about 0.1 mg/kg to about 100 mg/kg. The daily dose typically utilized for administration to a human subject is between about 25 and about 1200 mg, or between about 50 and about 1000 mg, or between about 50 and about 900 mg, or between about 100 and about 900 mg, or between about 100 and about 600 mg, or between about 150 and about 600 mg, or about 150 mg, or about 300 mg, or about 600 mg, or about 900 mg, or between 10 and 1500 mg, or between 25 and 1200 mg, or between 50 and 1000 mg, or between 50 and 900 mg, or between 100 and 900 mg, or between 100 and 600 mg, or between 150 and 600 mg, or 150 mg, or 300 mg, or 600 mg, or 900 mg. The daily dose can be by non-limiting example, 25 mg, or mg, or 35 mg, or 40 mg, or 45 mg, or 50 mg, or 55 mg, or 60 mg, or 65 mg, or 70 mg, or 75 mg, or 80 mg, or 85 mg, or 90 mg, or 95 mg, or 100 mg, 125 mg, or 150 mg, or 175 mg, or 200 mg, or 225 mg, or 250 mg, or 275 mg, or 300 mg, or 325 mg, or 350 mg, or 375 mg, or 400 mg, or 425 mg, or 450 mg, or 475 mg, or 500 mg, or 525 mg, or 550 mg, or 575 mg, or 600 mg, or 625 mg, or 650 mg, or 675 mg, or 700 mg, or 725 mg, or 750 mg, or 775 mg, or 800 mg, or 825 mg, or 850 mg, or 875 mg, or 900 mg, or 925 mg, or 975 mg, or 1000 mg, or 1025 mg, or 1050 mg, or 1075 mg, or 1100 mg, or 1125 mg, or 1150 mg, or 1175 mg, or 1200 mg. For gemcabene the preferred daily dose is 150 mg, or 300 mg, 600 mg or 900 mg. The compounds of the present disclosure may be administered 1, 2, 3, 4 or 5 times per day. Preferably the compounds are administered 1 or 2 times a day. More preferably the compounds are administered 1 time per day. In any of the foregoing embodiments the statin is atorvastatin, lovastatin, simvastatin, pravastatin, rosuvastatin, fluvastatin, pitavastatin or any combination thereof.

Another embodiment is a method of lowering the plasma LDL-C level in a patient on a stable dose of statin, comprising administering to the patient, an effective amount of a gemcabene. Another embodiment is a method of decreasing a patient's risk for developing coronary heart disease or having a recurrent cardiovascular event, comprising administering to the patient, an effective amount of a gemcabene. Yet another embodiment is a method of preventing, delaying the onset of, or reducing the severity of a secondary cardiovascular event, comprising administering to the patient, an effective amount of a gemcabene.

Another embodiment is a method of lowering the plasma LDL-C level in a patient on a stable dose of statin, comprising administering to the patient, an effective amount of a gemcabene, wherein the gemcabene is administered as a calcium salt. Another embodiment is a method of decreasing a patient's risk for developing coronary heart disease or having a recurrent cardiovascular event, comprising administering to the patient, an effective amount of a gemcabene, wherein the gemcabene is administered as a calcium salt. Yet another embodiment is a method of preventing, delaying the onset of, or reducing the severity of a secondary cardiovascular event, comprising administering to the patient, an effective amount of a gemcabene, wherein the gemcabene is administered as a calcium salt.

Another embodiment is a method of lowering the plasma LDL-C level in a patient on a stable dose of statin, comprising administering to the patient, an effective amount of a gemcabene, wherein the gemcabene is administered as a monocalcium salt. Another embodiment is a method of decreasing a patient's risk for developing coronary heart disease or having a recurrent cardiovascular event, comprising administering to the patient, an effective amount of a gemcabene, wherein the gemcabene is administered as a monocalcium salt. Yet another embodiment is a method of preventing, delaying the onset of, or reducing the severity of a secondary cardiovascular event, comprising administering to the patient, an effective amount of a gemcabene, wherein the gemcabene is administered as a monocalcium salt.

Another embodiment is a method of lowering the plasma LDL-C level in a patient on a stable dose of statin, comprising administering to the patient, an effective amount of a gemcabene and the daily dose is 150 mg, or 300 mg, 600 mg or 900 mg. Another embodiment is a method of decreasing a patient's risk for developing coronary heart disease or having a recurrent cardiovascular event, comprising administering to the patient, an effective amount of a gemcabene and the daily dose is 150 mg, or 300 mg, 600 mg or 900 mg. Yet another embodiment is a method of preventing, delaying the onset of, or reducing the severity of a secondary cardiovascular event, comprising administering to the patient, an effective amount of a gemcabene and the daily dose is 150 mg, or 300 mg, 600 mg or 900 mg.

Another embodiment is a method of lowering the plasma LDL-C level in a patient on a stable dose of statin, comprising administering to the patient, an effective amount of a gemcabene, wherein the gemcabene is administered as a calcium salt and the daily dose is 150 mg, or 300 mg, 600 mg or 900 mg. Another embodiment is a method of decreasing a patient's risk for developing coronary heart disease or having a recurrent cardiovascular event, comprising administering to the patient, an effective amount of a gemcabene, wherein the gemcabene is administered as a calcium salt and the daily dose is 150 mg, or 300 mg, 600 mg or 900 mg. Yet another embodiment is a method of preventing, delaying the onset of, or reducing the severity of a secondary cardiovascular event, comprising administering to the patient, an effective amount of a gemcabene, wherein the gemcabene is administered as a calcium salt and the daily dose is 150 mg, or 300 mg, 600 mg or 900 mg.

Another embodiment is a method of lowering the plasma LDL-C level in a patient on a stable dose of statin, comprising administering to the patient, an effective amount of a gemcabene, wherein the gemcabene is administered as a monocalcium salt and the daily dose is 150 mg, or 300 mg, 600 mg or 900 mg. Another embodiment is a method of decreasing a patient's risk for developing coronary heart disease or having a recurrent cardiovascular event, comprising administering to the patient, an effective amount of a gemcabene, wherein the gemcabene is administered as a monocalcium salt and the daily dose is 150 mg, or 300 mg, 600 mg or 900 mg. Yet another embodiment is a method of preventing, delaying the onset of, or reducing the severity of a secondary cardiovascular event, comprising administering to the patient, an effective amount of a gemcabene, wherein the gemcabene is administered as a monocalcium salt and the daily dose is 150 mg, or 300 mg, 600 mg or 900 mg.

It should be understood that a specific dosage and treatment regimen for any particular patient will depend upon a variety of factors, including the activity of the specific compound employed, the age, body weight, general health, sex, diet, time of administration, rate of excretion, drug combination and the judgment of the treating physician, and the severity of the particular disease being treated. The amount of the compound administered will also depend upon the particular compound in the composition.

With reference to any of the foregoing embodiments, preferred embodiments include where the compound of formula (I) is gemcabene, or the compound of formula (I) is the calcium salt of gemcabene, or the compound of formula (I) is the monocalcium salt of gemcabene.

Compounds useful in the present invention can be formulated as pharmaceutical compositions and administered to a subject, such as a human subject in a variety of forms adapted to the chosen route of administration, i.e., orally, transdermal, and parenterally, by intravenous, intramuscular, or subcutaneous routes. Such compositions and methods for their preparation are well known and may be found, for example, in Remington's Pharmaceutical Sciences, 19th Edition (Mack Publishing Company, 1995). For example, typical formulations for gemcabene are described in U.S. Pat. No. 5,648,387. In one embodiment, gemcabene is formulated with common excipients and carriers such as starch, binders, diluents and the like, and molded into tablets, or encapsulated into gelatin capsules, all for convenient oral administration. Gemcabene has excellent physical properties that enable formulation as syrups, elixirs, slow release lozenges and other common oral formulation types. Gemcabene can additionally be formulated with saline and other common excipients for administration by the intravenous route, intraperitoneal and similar parenteral routes. Transdermal patches can be made with binders and common adjuvants, and rectal formulations using pharmaceutically acceptable waxes can be made utilizing common formulation technologies that are well known to those skilled in the art of pharmaceutical formulations.

The number of references relating to lowering of LDL-C is great and the parameters in the studies can be very different. The discussion of the references below is not meant to be exhaustive but rather to illustrate the art regarding two points that are particularly relevant to the interpretation of the data in the present application. The first being that the lowering of LDL-C is not a linear process. Doubling the dose of LDL-C lowering agent does not necessarily result in a doubling of LDL-C lowering. Second, statins are very effective in lowering LDL-C and additional lowering seen beyond that of a statin is generally minimal, from about 1% to about 17%, as discussed in the references discussed below.

McKenney J. M., Am. J. Ther. (2004), Vol. 11, pp 55-59, notes that "Statins have a nonlinear dose-response relationship, such that doubling the dose of a particular statin will provide a further reduction in LDL-C of approximately 6%." Pauciullo, P. et al. (Atherosclerosis (2000), Vol. 150, pp 429-436, at page 432), discloses data regarding cholesterol lowering with the combination of fluvastatin and bezafibrate. Fluvastatin (40 mg) alone gave LDL-C lowering of 22.5% and bezafibrate (400 mg) alone gave a lowering of 9.6%. The combination provided only a 23.6% lowering- an incremental change of only 1.1% (not statistically significant). Illingworth and Bacon (Circulation (1989); Vol. 79, pp 590-596, at page 593), lovastatin (40 mg twice daily) lowered LDL-C by 35.5% where as lovastatin+gemfibrozil (600 mg twice daily) lowered LDL-C by 39.6% providing only an additional LDL-C lowering of 4.1% (not statistically significant). Jones, P. H. (Clin. Lipidol. (2009), Vol. 4(6), pp 699-711) reported that the addition of 135 mg of fenofibrate to a low dose of statin raised LDL-C levels from −39.9% (statin alone) to −33.1%, a difference of 0.8% (not statistically significant). Jones also reported that the addition of 135 mg of fenofibrate to a moderate dose of statin raised LDL-C levels from −40.6% (statin alone) to −34.6%, a difference of 5.1%. A combination of ezetimibe and statin showed a greater affect. Stein, E., Eur. Heart J. Suppl. (2001); Vol. 3 (suppl E), pp E11-16, reported that as a monotherapy simvastatin, 10 mg, lowered LDL-C by 35% and ezetimibe, 10 mg, lowered LDL-C by 16% while the combination of simvastatin and ezetimibe (a cholesterol absorption inhibitor) lowered LDL-C by 52%, a difference of 17%.

EXAMPLES

Example 1

Gemcabene Further Lowers LDL-C in Patients not Reaching Goal on Statin Therapy

An 8-week, double-blind, placebo-controlled, randomized, multicenter, phase 2 study in hypercholesterolemic patients on a stable dose of statin (on statin therapy for at least the previous 3 months) was conducted to evaluate the efficacy of gemcabene in the further reduction of LDL-C in these patients.

A total of 66 hypercholesterolemic patients were treated in this study: 22 randomized to gemcabene 900 mg, 20 randomized to gemcabene 300 mg, and 24 randomized to placebo.

Patients included in the study were men and women ≥18 and ≤565 years of age with hypercholesterolemia and an LDL-C level at screening of ≥130 mg/dL while on a stable (3-months) dose of a statin. Patients were required to maintain their current dose of statin throughout the course of the study.

Patients were excluded for any of the following reasons: women with childbearing potential; ages >65 and <18 years; triglycerides >400 mg/dL; creatinine phosphokinase levels >3 times the upper limit of normal (ULN); body mass index >35; any of the following within 1 month of enrolling into the study: myocardial infarction, severe or unstable angina pectoris, coronary angioplasty, coronary artery bypass graft, or any other major cardiovascular event resulting in hospitalization; uncontrolled diabetes mellitus ($HbA_{1c}$, >10%), renal dysfunction, hepatic dysfunction, history of gall stones or gall bladder disease; known hypersensitivity to a lipid-altering agent; participation in another clinical study concurrently or within 30 days prior to the screening visit; taking excluded medications/supplements, abnormalities investigator feels may compromise the patient's safety or successful participation in the study.

Study medication in tablet form was taken orally during the 8-week double-blind phase of the study. Patients were randomized to 1 of 3 treatment groups: Placebo plus concomitant statin, gemcabene 300 mg QD plus concomitant statin, and gemcabene 900 mg QD plus concomitant statin. The dose of concomitant statin therapy was to remain constant throughout the study.

Percent change from base line was calculated as follows:

Percent Change From Baseline=[(final value−baseline value)/baseline value]×100%.

Baseline values were defined as the mean of the 2 lipid measurements obtained at screening and Week 0. Final lipid values were obtained at week 8.

LDL-C Efficacy Results: gemcabene at 300 and 900 mg per day significantly lowered LDL-C from baseline at Week 8 by a median of 24.8% and 31.0% respectively, compared with a placebo reduction of 7.9% (both p<0.01). Results are shown in Table 3.

These data are particularly surprising in view of a previous published study that showed that co-administration of 300, 600, and 900 mg gemcabene with atorvastatin (aggregated over the dose range of 10, 40 and 80 mg of atorvastatin) resulted in a decrease in LDL-C beyond atorvastatin monotherapy of 3.8%, 6.1% and 7.4% respectively (see Mandema et al., AAPS Journal 2005; 7(3) Article 52).

TABLE 3

Percent Change From Baseline in LDL-C at Week 8[a]

| Lipid Parameter | Placebo + Statin | gemcabene + Statin | |
|---|---|---|---|
| | | 300 mg QD | 900 mg QD |
| N | N = 22 | N = 18 | N = 21 |
| Median Baseline | 153.3 | 143.5 | 142.5 |
| Median Week 8 | 137 | 101.5 | 103 |
| Median % change | −7.9 | −24.8 | −31.0 |
| p-Value | N/A | 0.005 | <0.001 |

[a]Evaluable patients only, Week 8 of double-blind treatment or last observation carried forward (LOCF) if Week 8 is missing The patients' Framingham Risk Score was calculated at baseline. The Framingham risk score calculation takes into account: age, gender, systolic blood pressure level (+/− treatment), HDL cholesterol level, and smoker status. After eight weeks, the Framingham Risk Score was reassessed and showed significant improvement in both statin plus gemcabene groups but not in the statin plus placebo group. Significance was determined using the SAS Proc Univariate which provides p values from the student's paired t-test and the Wilcoxon Signed Rank test.

Framingham Results: As shown in Table 4, treatment with gemcabene at 300 mg and 900 mg QD significantly reduced the Framingham Risk Score compared with statin treatment alone.

TABLE 4

Reduction in Framingham Risk Score with Gemcabene Treatment

| Lipid Parameter | Placebo + Statin | gemcabene + Statin | |
|---|---|---|---|
| | | 300 mg QD | 900 mg QD |
| N | N = 24 | N = 19 | N = 19 |
| Risk Points Mean difference | 0.75 | 1.95 | 3.21 |
| p-Value Student's paired t-test | 0.1279 | 0.0068 | <0.0001 |
| p-Value Signed Rank | 0.1519 | 0.0061 | <0.0001 |

The invention claimed is:

1. A method of treating a patient on a stable dose of statin comprising administering to the patient the compound:

(gemcabene)

or a salt, or a hydrate thereof, wherein the patient on a stable dose of statin requires additional lowering of LDL-C; wherein the daily dose of the compound administered is from about 100 mg to about 900 mg; and wherein following treatment, the patient's LDL-C level is reduced.

2. The method of claim 1, wherein the patient's LDL-C level is reduced from baseline by at least 20%.

3. The method of claim 2, wherein the patient's LDL-C level is reduced from baseline by at least 30%.

4. The method of claim 1, wherein the daily dose is administered once daily.

5. The method of claim 4, wherein the daily dose is from about 300 mg to about 900 mg.

6. The method of claim 5, wherein the daily dose is 300 mg, 600 mg or 900 mg.

7. The method of claim 1, wherein the stable dose of statin is from about 1 mg to about 80 mg administered daily.

8. The method of claim 7, wherein the statin is atorvastatin, lovastatin, simvastatin, pravastatin, rosuvastatin, fluvastatin, or pitavastatin.

9. The method according to claim 8, wherein the statin is atorvastatin and the stable dose of statin is from about 10 mg to about 80 mg.

10. The method according to claim 8, wherein the statin is rosuvastatin and the stable dose of statin is from about 2.5 to about 40.

11. The method according to claim 8, wherein the statin is simvastatin and the stable dose of statin is from about 10 mg to about 80 mg.

12. The method according to claim 4, wherein the patient is administered one or more additional cholesterol lowering drug independently selected from the group consisting of: a cholesterol absorption inhibitor, a bile acid sequestrant, a cholesteryl ester transfer protein inhibitor, a microsomal triglyceride transfer protein inhibitor, a PCSK9 inhibitor, a microRNA-33 inhibitor, a squalene synthase inhibitor and an apoB synthesis inhibitor.

13. The method according to claim 1, wherein the patient has a baseline LDL-C level ≥70 mg/dL.

14. The method according to claims 13, wherein the patient has a baseline LDL-C level level ≥100 mg/dL.

15. The method according to claim 1, wherein the patient's LDL-C level is reduced from baseline by at least 15%.

16. A method of treating a patient on a maximally tolerated dose of a statin comprising administering to the patient the compound:

(gemcabene)

or a salt, or a hydrate thereof, wherein the patient on a maximally tolerated dose of a statin requires additional lowering of LDL-C; wherein the daily dose of the compound administered is from about 100 mg to about 900 mg; and wherein following treatment the patient's LDL-C level is reduced.

17. The method according to claim 16, wherein the patient's LDL-C level is reduced from baseline by at least 15%.

18. The method of claim 16, wherein the patient's LDL-C level is reduced from baseline by at least 20%.

19. The method of claim 16, wherein the patient's LDL-C level is reduced from baseline by at least 30%.

20. The method of claim 16, wherein the daily dose is administered once daily.

21. The method of claim 20, wherein the daily dose is from about 300 mg to about 900 mg.

22. The method of claim 21, wherein the daily dose is 300 mg, 600 mg or 900 mg.

23. The method of claim 16, wherein the stable dose of statin is from about 1 mg to about 80 mg administered daily.

24. The method of claim 23, wherein the statin is atorvastatin, lovastatin, simvastatin, pravastatin, rosuvastatin, fluvastatin, or pitavastatin.

25. The method according to claim 16, wherein the statin is atorvastatin and the stable dose of statin is from about 10 mg to about 80 mg.

26. The method according to claim 16, wherein the patient has a baseline LDL-C level ≥70 mg/dL.

27. The method according to claims 16, wherein the patient has a baseline LDL-C level >100 mg/dL.

* * * * *